United States Patent
Hutchinson et al.

(10) Patent No.: US 10,909,678 B2
(45) Date of Patent: Feb. 2, 2021

(54) METHOD AND APPARATUS FOR MONITORING OF A HUMAN OR ANIMAL SUBJECT

(71) Applicant: OXEHEALTH LIMITED, Oxford (GB)

(72) Inventors: Nicholas Dunkley Hutchinson, Oxford (GB); Oliver John Gibson, Oxford (GB); Peter Richard Dodds, Oxford (GB)

(73) Assignee: OXEHEALTH LIMITED, London (GB)

( * ) Notice: Subject to any disclaimer, the term of this patent is extended or adjusted under 35 U.S.C. 154(b) by 0 days.

(21) Appl. No.: 16/291,728

(22) Filed: Mar. 4, 2019

(65) Prior Publication Data
US 2019/0272635 A1    Sep. 5, 2019

(30) Foreign Application Priority Data
Mar. 5, 2018    (GB) .................................. 1803508.9

(51) Int. Cl.
*G06F 3/0481*  (2013.01)
*H04N 7/18*    (2006.01)
(Continued)

(52) U.S. Cl.
CPC ........ *G06T 7/0012* (2013.01); *A61B 5/02416* (2013.01); *A61B 5/1128* (2013.01);
(Continued)

(58) Field of Classification Search
CPC .............. G06T 7/12; G06T 7/20; H04N 7/183
(Continued)

(56) References Cited

U.S. PATENT DOCUMENTS 8,855,384 B2    10/2014   Kyal et al.
8,965,090 B1     2/2015   Khachaturian et al.
(Continued)

FOREIGN PATENT DOCUMENTS

EP    0615245 A2    9/1994
EP    0919184 A1    6/1999
(Continued)

OTHER PUBLICATIONS

Verkruysse et al., Remote Plethysmographic Imaging Using Ambient Light, Optics Express, 16(26), Dec. 22, 2008 pp. 21434-21445.
(Continued)

*Primary Examiner* — Amir Shahnami
(74) *Attorney, Agent, or Firm* — Harness, Dickey & Pierce, P.L.C.

(57) ABSTRACT

A method and apparatus for monitoring a human or animal subject in a room using video imaging of the subject and analysis of the video image to derive an estimate of vital signs such as heart rate or breathing rate. The method includes determination of whether the subject in the images is still or moving, and whether any of the regions from which vital signs are being detected are not on the subject. The subject's movement may be manually or automatically detected, and the determination of whether regions from which vital signs are being detected are not on the subject can be input manually, by displaying the regions to the user in a visually distinguishable manner, or automatically. Vital signs measurements are only displayed if the subject is determined as being still and if there are no regions in the image which are returning vital signs signals but are not determined as being on the subject.

12 Claims, 4 Drawing Sheets

(51) Int. Cl.
 *A61B 5/11* (2006.01)
 *G06T 7/00* (2017.01)
 *G06F 3/0482* (2013.01)
 *G06T 7/20* (2017.01)
 *A61B 5/00* (2006.01)
 *A61B 5/024* (2006.01)

(52) U.S. Cl.
 CPC .......... *A61B 5/6889* (2013.01); *G06F 3/0482* (2013.01); *G06F 3/04817* (2013.01); *G06T 7/20* (2013.01); *H04N 7/183* (2013.01); *G06T 2200/24* (2013.01); *G06T 2207/10016* (2013.01); *G06T 2207/20104* (2013.01); *G06T 2207/30196* (2013.01); *G06T 2207/30232* (2013.01)

(58) Field of Classification Search
 USPC .......................................................... 348/77
 See application file for complete search history.

(56) References Cited

U.S. PATENT DOCUMENTS

| | | | |
|---|---|---|---|
| 9,036,877 | B2 | 5/2015 | Kyal et al. |
| 10,034,979 | B2 | 7/2018 | Bechtel et al. |
| 10,292,662 | B2 | 5/2019 | Kirenko |
| 2002/0106709 | A1 | 8/2002 | Potts et al. |
| 2002/0180870 | A1 | 12/2002 | Chen |
| 2003/0138149 | A1 | 7/2003 | Iizuka et al. |
| 2003/0228032 | A1 | 12/2003 | Rui et al. |
| 2005/0197590 | A1 | 9/2005 | Osorio et al. |
| 2006/0058618 | A1 | 3/2006 | Nishiura |
| 2006/0074321 | A1* | 4/2006 | Kouchi ................ G01D 7/005 600/481 |
| 2007/0156060 | A1 | 7/2007 | Cervantes |
| 2007/0195931 | A1 | 8/2007 | Ohishi |
| 2008/0292151 | A1 | 11/2008 | Kurtz et al. |
| 2009/0216499 | A1 | 8/2009 | Tobola et al. |
| 2010/0049064 | A1 | 2/2010 | Bodmer et al. |
| 2010/0074475 | A1 | 3/2010 | Chouno |
| 2010/0298656 | A1 | 11/2010 | McCombie et al. |
| 2011/0046498 | A1 | 2/2011 | Klap et al. |
| 2011/0150274 | A1 | 6/2011 | Patwardhan et al. |
| 2011/0251493 | A1 | 10/2011 | Poh et al. |
| 2011/0311143 | A1 | 12/2011 | Cennini et al. |
| 2012/0141000 | A1 | 6/2012 | Jeanne et al. |
| 2012/0213405 | A1 | 8/2012 | Saskil |
| 2012/0242819 | A1 | 9/2012 | Schamp |
| 2013/0138009 | A1 | 5/2013 | Nierenberg et al. |
| 2013/0324875 | A1 | 12/2013 | Mestha et al. |
| 2014/0003690 | A1 | 1/2014 | Razeto et al. |
| 2014/0023235 | A1 | 1/2014 | Cennini et al. |
| 2014/0037163 | A1 | 2/2014 | Kirenko et al. |
| 2014/0037166 | A1 | 2/2014 | De Haan et al. |
| 2014/0236036 | A1 | 8/2014 | de Haan et al. |
| 2014/0276099 | A1 | 9/2014 | Kirenko et al. |
| 2014/0276104 | A1 | 9/2014 | Tao et al. |
| 2014/0334697 | A1 | 11/2014 | Kersten et al. |
| 2014/0371599 | A1 | 12/2014 | Wu et al. |
| 2014/0371635 | A1 | 12/2014 | Shinar et al. |
| 2014/0378842 | A1 | 12/2014 | Xu et al. |
| 2015/0005646 | A1 | 1/2015 | Balakrishnan et al. |
| 2015/0063708 | A1 | 3/2015 | Sripadarao et al. |
| 2015/0148687 | A1 | 5/2015 | Kitajima et al. |
| 2015/0208987 | A1 | 7/2015 | Shan et al. |
| 2015/0221069 | A1 | 8/2015 | Shaburova et al. |
| 2015/0250391 | A1 | 9/2015 | Kyal et al. |
| 2015/0363361 | A1 | 12/2015 | Kniazev |
| 2016/0106340 | A1 | 4/2016 | Mestha et al. |
| 2016/0125260 | A1 | 5/2016 | Huang et al. |
| 2016/0132732 | A1 | 5/2016 | Gunther et al. |
| 2016/0220128 | A1 | 8/2016 | Den Brinker et al. |
| 2016/0253820 | A1 | 9/2016 | Jeanne et al. |
| 2016/0310067 | A1 | 10/2016 | Heinrich et al. |
| 2017/0007185 | A1* | 1/2017 | Lin ........................ A61B 5/721 |
| 2017/0042432 | A1 | 2/2017 | Adib et al. |
| 2017/0224256 | A1 | 8/2017 | Kirenko |
| 2017/0238805 | A1 | 8/2017 | Addison et al. |
| 2017/0238842 | A1* | 8/2017 | Jacquel ................ A61B 5/743 |
| 2018/0085010 | A1 | 3/2018 | Jones et al. |
| 2018/0279885 | A1 | 10/2018 | Bulut |
| 2019/0000391 | A1 | 1/2019 | De Haan et al. |
| 2019/0267040 | A1* | 8/2019 | Ikeda ....................... H04N 5/91 |

FOREIGN PATENT DOCUMENTS

| | | |
|---|---|---|
| EP | 1571594 A2 | 9/2005 |
| EP | 2767233 A1 | 8/2014 |
| EP | 2976998 A1 | 1/2016 |
| EP | 2988274 A2 | 2/2016 |
| EP | 3073905 A1 | 10/2016 |
| EP | 3207862 A1 | 8/2017 |
| JP | 2011130996 A | 7/2011 |
| WO | WO-2010/100593 A1 | 9/2010 |
| WO | WO-2010/115939 A2 | 10/2010 |
| WO | WO-2011021128 A2 | 2/2011 |
| WO | WO-2013027027 A2 | 2/2013 |
| WO | WO-2014125250 A1 | 8/2014 |
| WO | WO 2014131850 A1 | 9/2014 |
| WO | WO 2014140994 A1 | 9/2014 |
| WO | WO-201504915 A1 | 1/2015 |
| WO | WO-2015049150 A1 | 4/2015 |
| WO | WO-2015055709 A1 | 4/2015 |
| WO | WO-2015/078735 A1 | 6/2015 |
| WO | WO-2015/091582 A1 | 6/2015 |
| WO | WO-2015172735 A1 | 11/2015 |
| WO | WO-2016092290 A1 | 6/2016 |
| WO | WO-2016094749 A1 | 6/2016 |
| WO | WO-2016159151 A1 | 10/2016 |
| WO | WO-2017125743 A1 | 7/2017 |
| WO | WO-2017125744 A1 | 7/2017 |
| WO | WO-2017125763 A1 | 7/2017 |

OTHER PUBLICATIONS

Distance PPG: Robust Non-Contact Vital Signs Monitoring Using a Camera by Mayank Kumar et al; Apr. 6, 2015; Biomedical Optics Express 1565, May 1, 2015, vol. 6 No. 5.
Pisani-Real-time Automated Detection of Clonic Seizures in Newborns, Clinical Neurophysiology 125 (2014) 1533-1540.
European Search Report regarding Application No. EP 19 15 8085 dated Jul. 10, 2019.
Nathalie M. El Nabbout et al, "Automatically Detecting and Tracking People Walking through a Transparent Door with Vision", Computer and Robot Vision, 2008. CRV '08. Canadian Conference on, IEEE, Piscataway, NJ, USA, May 28, 2008 (May 28, 2008), pp. 171-178.
Qiang Zhu et al, "Learning a Sparse, Corner-Based Representation for Corner-Based Representation for Time-varying Background Modeling", Computer Vision, 2005. ICCV 2005. Tenth IEEE International Conference on Beijing, China Oct. 17-20, 2005, Piscataway, NJ, USA, IEEE, Los Alamitos, CA, USA, vol. 1, Oct. 17, 2005 (Oct. 17, 2005), pp. 678-685.
Konstantinos Avgerinakis et al, "Activity detection and recognition of daily living events", Proceedings of the 1st ACM International Workshop on Multimedia Indexing and Information Retrieval for Healthcare, MIIRH '13, Oct. 22, 2013 (Oct. 22, 2013), pp. 1-7.
Arindam Sikdar et al, "Computer-Vision-Guided Human Pulse Rate Estimation: A Review", IEEE Reviews in Biomedical Engineering, vol. 9, Sep. 16, 2016 (Sep. 16, 2016), pp. 91-105.
Yu Sun et al,"Photoplethysmography Revisited: From Contact to Noncontact, From Point to Imaging", IEEE Transactions on Biomedical Engineering, IEEE Service Center, Piscataway, NJ, USA, vol. 63, No. 3, Mar. 1, 2016 (Mar. 1, 2016), pp. 463-477.
Tongchi Zhou et al, "A study of relative motion point trajectories for action recognition", 2015 International Conference on Wireless Communications & Signal Processing (WCSP), IEEE, Oct. 15, 2015 (Oct. 15, 2015), pp. 1-5.
Hisato Aota et al, "Extracting objects by clustering of full pixel trajectories", Signal Processing and Multimedia Applications (SIGMAP), Proceedings of the 2010 International Conference on, IEEE, Jul. 26, 2010 (Jul. 26, 2010), pp. 65-72.

(56) References Cited

OTHER PUBLICATIONS

Shandong Wu et al, "A hierarchical motion trajectory signature descriptor", 2008 IEEE International Conference on Robotics and Automation. The Half-Day Workshop on: Towards Autonomous Agriculture of Tomorrow, IEEE—Piscataway, NJ, USA, Piscataway, NJ, USA, May 19, 2008 (May 19, 2008), pp. 3070-3075.
Search Report for GB Application No. 1618828.6, dated Mar. 31, 2017.
International Search Report and Written Opinion for PCT/GB2017/053343, dated Jan. 4, 2018; ISA/EP.
International Search Report and Written Opinion for PCT/GB2017/052779, dated Nov. 10, 2017; ISA/EP.
Search Report for GB Application No. 1615899.0, dated Feb. 28, 2017.
International Preliminary Report on Patentability and Written Opinion regarding Applicaiton No. PCT/GB2017/052779 dated Mar. 19, 2019.
International Search Report for PCT/GB2017/050162, ISA/EP, Rijswijk, NL, dated Jul. 6, 2017.
Written Opinion of the ISA for PCT/GB2017/050162, ISA/EP, Rijswijk, NL, dated Jul. 6, 2017.
Search Report for Priority Application GB1601140.5, UK IPO, Newport, South Wales, dated Jul. 21, 2016.
International Search Report for PCT/GB2017/050127, ISA/EP, Rijswijk, NL, dated Mar. 28, 2017.
Written Opinion of the ISA for PCT/GB2017/050127, ISA/EP, Rijswijk, NL, dated Mar. 28, 2017.
UK IPO Search Report under Section 17(5) for priority application GB1061143.9, dated Mar. 30, 2016.
International Search Report for PCT/GB2017/050128, ISA/EP, Rijswijk, NL, dated Apr. 13, 2017.
Written Opinion of the ISA for PCT/GB2017/050128, ISA/EP, Rijswijk, NL, dated Apr. 13, 2017.
Search Report under Section 17(5) for priority application GB1601142.1, UKIPO, Newport, South Wales, dated Jun. 28, 2016.
Tarassenko et al, "Non-contact video-based vital sign monitoring using ambient light and auto-regressive models", 2014 Physiol. Meas. 35 807, pp. 807-831.
Wu et al, Eulerian Video Magnification for Revealing Subtle Changes in the World, 2012.
International Search Report for PCT/GB2017/050126, ISA/EP, Rijswijk, NL, dated Apr. 20, 2017.
Written Opinion of the ISA for PCT/GB2017/050126, ISA/EP, Rijswijk, NL, dated Apr. 20, 2017.
UK IPO Search Report for GB priority application 1601217.1, Newport, South Wales, dated Jul. 25, 2016.
Search Report regarding United Kingdom Patent Application No. GB1706449.4, dated Oct. 25, 2017.
Amelard Robert et al. "Illumination-compensated non-contact imaging photoplethysmography via dual-mode temporally coded illumination". Progress in Biomedical Optics and Imaging, SPIE—International Society for Optical Engineering, Bellingham, WA, US., vol. 9316, Mar. 5, 2015.
Blocker Timon et al, "An online PPGI approach for camera based heart rate monitoring using beat-to-beat detection", 2017 IEEE Sensors Applications Symposium (SAS), IEEE, Mar. 13, 2017.
Extended European Search Report regarding applicaiton No. 18168310.3-1115 dated Oct. 1, 2018.
Nakajima, Kazuki, Yoshiaki Matsumoto, and Toshiyo Tamura. "Development of real-time image sequence analysis for evaluating posture change and respiratory rate of a subject in bed." Physiological Measurement 22.3 (2001).
Search Report of UKIPO regarding Application No. GB1900033.0 dated Jun. 13, 2019.
British Search Report regarding Appliction No. 1900034.8 dated Jun. 13, 2019.
Extended EP Search Report regarding Application No. 19220090.5 dated Feb. 24, 2020.
U.S. Appl. No. 16/732,769, filed Jan. 2, 2020, Nicholas Dunkley Hutchinson.
U.S. Appl. No. 16/732,979, dated Jan. 2, 2020, Nicholas Dunkley Hutchinson.
U.S. Appl. No. 16/733,065, filed Jan. 2, 2020, Nicholas Dunkley Hutchinson.
U.S. Appl. No. 15/961,279, filed Apr. 24, 2018, Nicholas Dunkley Hutchinson.
U.S. Appl. No. 16/071,542, filed Jul. 20, 2018, Nicholas Dunkley Hutchinson.
U.S. Appl. No. 16/071,570, filed Jul. 20, 2018, Simon Mark Chave Jones.
U.S. Appl. No. 16/071,591, filed Jul. 20, 2018, Muhammad Fraz.
U.S. Appl. No. 16/071,611, filed Jul. 20, 2018, Nicholas Dunkley Hutchinson.
U.S. Appl. No. 16/334,211, filed Mar. 18, 2019, Mohamed Elmikaty.
U.S. Appl. No. 16/347,925, filed May 7, 2019, Simon Mark Chave Jones.

\* cited by examiner

METHOD AND APPARATUS FOR MONITORING OF A HUMAN OR ANIMAL SUBJECT

CROSS-REFERENCE TO RELATED APPLICATIONS

This application claims the benefit of Great Britain Patent Application No. 1803508.9, filed Mar. 5, 2018. The entire disclosure of the above application is incorporated herein by reference.

FIELD

The present invention relates to a method and apparatus for monitoring a human or animal subject, and in particular a subject within an enclosed area, e.g. a room such as a secure room.

BACKGROUND

There are many situations where a subject is in an enclosed environment, such as a room in a hospital, secure room in a prison or hospital, or even a home environment, where a duty of care is placed on an authority responsible for the subject. To comply with such duty of care requirements, it is conventional to monitor subjects in such environments. Such monitoring may comprise regular, scheduled visual checks by a member of staff and/or continuous video monitoring of the subject in the room. While such monitoring can be effective, difficulties can arise with the subject's health changing quickly between scheduled checks, or with a lack of movement of the subject being misinterpreted. For example, a subject who is lying still on a bed or on the floor may be resting or asleep, or may have a suffered a deterioration in health. Subjects who are under the influence of alcohol or drugs or suffering a mental condition may behave in ways which are abnormal and difficult for staff observing them to interpret correctly. It would therefore be useful to have a way of monitoring the subject which provides an indication of their health.

Monitoring of vital signs offers the possibility of mitigating some of these problems, but traditional contact-based vital signs sensors are restrictive and inconvenient, and some subjects may not co-operate with their use. Recent developments demonstrating that vital signs such as heart rate or breathing rate can be detected in video images of the human body, where the video images are obtained using a standard video camera, are of significant interest. For example Verkruysse et al., "Remote plethysmographic imaging using ambient light", Optics Express, 16 (26), 22 Dec. 2008, PP. 21434-21445 demonstrated that changes in reflectivity or transmittivity of the subject's skin caused by cardiac synchronous variations in the volume of oxygenated blood in the skin capillaries, known as photoplethysmographic image or PPGi signals, could be detected in the video signal from a conventional consumer standard video camera where a human subject was illuminated under ambient light. This idea has been developed further in, for example, WO-A2-2013/027027, WO-A-2011/021128 and WO-A1-2015/049150 which aim to increase the reliability of the detection of the remote PPG signal.

The paper "Distance PPG: robust non-contact vital signs monitoring using a camera" by Mayank Kumar et al.; 6 Apr. 2015; Biomedical Optics Express 1565, 1 May 2015, Vol. 6 No. 5, discusses a method of combining skin-colour change signals from different tracked regions of a subject's face using a weighted average, where the weights depend on the blood perfusion and incident light density in the region to improve the signal-to-noise ratio of the camera-based estimate. It discusses the various challenges for camera-based non-contact vital sign monitoring and proposes that improvements in the signal-to-noise ratio of the camera-based estimates reduces the errors in vital sign estimation.

Many of the prior art techniques have been based on careful control of the subject being monitored and the lighting conditions in the environment. Thus, although they claim success in detecting the heart rate or vital signs of the subject, in general the subjects were required to remain relatively still, the subjects were not obscured and the lighting conditions were kept relatively constant.

Other techniques based on detecting fine movement associated with breathing or heart beat or a combination of movement and PPGi have also been proposed. In the health and security monitoring fields proposals have also been made for detecting and classifying the gross movement of subjects in a video image as dangerous or non-dangerous, for example the proposal for detecting clonic seizures as described in the paper "Real-time automated detection of clonic seizures in newborns" by Pisani et al.

Another common problem with such video image analysis is finding and tracking the subject in the video image. The human body is naturally deformable and the orientation of the subject with respect to camera's view point can vary significantly. Also the subjects may be still, in which case motion-based detection and tracking can fail, or may move significantly or in unpredictable ways, which can be difficult for feature-based techniques. Even in a relatively simple visual scene, such as a single human subject in a fairly plain room (as may be found in care or secure institutions such as hospitals, care homes, detention centres or prisons), subjects may be covered with bedclothes, which can make them difficult to detect automatically, and actions such as throwing bedclothes across the room can cause image features which were previously associated with the subject to move across the image and thus be tracked, despite the fact that they are not of interest. Subjects mix periods of high activity and large movement with periods of relative immobility (seated or lying), will in general be clothed and have bedding to cover themselves. Thus, periods of inactivity while lying down, may coincide with the subject covering themselves partly or completely (known as "tenting") with bedding. Further, illumination may vary between daylight and artificial light and secure rooms are sometimes lit with visible artificial light and are sometimes completely dark, with infrared being the only illumination available. Other sources of regular or irregular movement may also appear in the scene being monitored—e.g. insects flying in, ventilation fans, domestic appliances Also, the arrangement of the video monitoring apparatus itself may cause difficulty for the video analysis. For safety reasons the video camera or cameras have to be positioned out of reach of the subject, normally high in a corner of the room. This means that the view of the subject tends to compressed by perspective and the subject is only a relatively small fraction of the field of view. Further, because the monitoring has to continue in the dark (when the subject is asleep), it is normal to use a monochrome infrared camera, which means that techniques relying on full colour images do not work.

In the context of monitoring the health and welfare of subjects for whom an institution may have a duty of care, the reliability of the system in real conditions is paramount, otherwise the system cannot be relied upon as helping discharge the institution's duty of care.

Existing systems do not provide monitoring, including vital signs monitoring such as heart or breathing rate detection, which operates reliably in the face of these difficulties associated with the wide variety of poorly-controlled settings in which such monitoring may be used.

Similar problems of movement and variable illumination occur also in other fields such as fitness and health and well-being in the home or elsewhere.

Being able to monitor a subject in these less controlled conditions and provide practically useful information would significantly improve the ability to monitor the well-being of such a subject and to comply with duty of care requirements, particularly in the health or security field. As with all monitoring systems, the primary need is to avoid excessive false alarming and also to avoid excessive under alarming. Excessive false alarming leads to monitoring systems being ignored by staff, or switched off. Excessive under alarming leads to a lack of trust in the system and does not meet the basic requirements of the monitoring system.

SUMMARY

The present invention therefore provides a method of monitoring a human or animal subject comprising the steps of: capturing a video image of the subject; analysing the video image to determine one or more vital signs of the subject; displaying to a user a graphical user interface comprising an icon indicative of the monitoring of the subject; determining whether the subject is still; if the subject is determined as still, determining whether all regions of the video image from which vital signs are detected are on the subject; if all regions of the video image from which vital signs are detected are on the subject, displaying the determined vital signs.

The method therefore provides for a verification step that the subject is in the image and that the subject is still, such that the vital signs measurement can be expected to be valid, or moving, meaning that the vital signs estimation may not be valid but that the subject is alive. This also means that rather than simply presenting vital signs, the method inherently includes some form of status and identity check of the subject. Further, because it is established that the vital signs measured in the video image are coming from the subject, rather than extraneous signal sources which may resemble the periodic signals representative of vital signs, the vital signs measurement is more reliable. For example, the method would not be confused by the presence of a fan or some other powered equipment generating periodic movement or periodic intensity variations.

In one embodiment the step of determining whether the subject is still comprises displaying a video image of the subject to the user and asking the user to input whether or not the subject is still. Thus the graphical user interface displays a request for the user to input their determination of whether the subject is still or moving. In an alternative embodiment the subject may be automatically detected in the image, for example using a conventional single shot detection (SSD) algorithm, with corresponding automatic detection of whether the subject is still or moving. Movement may be automatically detected by using a technique such as that in the paper by Pisani et al mentioned above or other techniques such as calculating the differences in pixels between consecutive frames or tracking the movements of features in the images.

The step of determining whether regions of the video image from which vital signs are detected are not on the subject may comprise displaying a video image of the subject with an indication in the displayed image of where vital signs are detected. For example, regions of interest used by the algorithm for detecting vital signs may be displayed in a visually distinguishable way, for example by outlining them or by changing their intensity or colour. Alternatively, icons may be overlaid over the entire regions of interest, or over their centre. The regions of interest may be displayed as shapes, such as regular geometric shapes, e.g. circles, rectangles, ovals, ellipses, whose centres indicate the centre of mass of a set of highly correlated vital sign signals. The regions of interest may be displayed as shapes whose centres indicate the centre of mass of a set of highly correlated vital sign signals, weighted by the strength of the signals. The size of the shapes, e.g. where the shapes are circles, their radii, may indicate the spatial distribution of the signals.

In one embodiment the graphical user interface displays a request to the user to input the result of a user determination of whether the regions of the image from which vital signs are being detected are on the subject or not, or more particularly whether there all such regions are on the subject. In an alternative embodiment, the presence of regions from which vital signs are being detected that are not on the subject can be conducted automatically, using the same automatic detection of the human subject in the image as mentioned above.

In one embodiment, upon selection by the user of the icon indicating monitoring of the subject, the method may further comprise: displaying a menu of selectable steps, one of said selectable steps being to take an observation of the vital signs of the subject; and upon selection of the step of taking an observation of the vital signs of the subject, performing the steps of determining if the subject is still and if all areas producing vital signs signals are on the subject.

In another embodiment of the invention, the method is extended to monitor a plurality of subjects simultaneously. For example, the graphical user interface may display an icon corresponding to each subject or room, with the user being able to select an individual icon and thus access the monitoring for that subject or room. The icons may simply indicate the room or subject, or may inherently include an indication of the status of the subject or room. For example, they may indicate whether or not the room is occupied by a human or animal subject, they may indicate a current estimate of the status of the subject, such as moving or not moving, and optionally may indicate a health status based on vital signs detection.

Another aspect of the invention provides apparatus for monitoring a subject in a room, the apparatus comprising a video camera configured to capture a video image sequence of the subject in the room, a data processor configured to automatically process the video image as specified above, and a display for displaying the output, the apparatus executing the method above.

The video camera may be a standard digital video camera so that the video image sequence is a conventional frame sequence with each frame comprising a spatial array of pixels of varying intensities and/or colours. The camera may be monochrome or may be a colour camera providing pixel intensities in the red, green and blue channels.

The video image sequence may be time-windowed, i.e. divided into batches of successive frames for processing, and the steps of subject tracking, movement measurement and vital signs estimation are conducted on the time windows. The time windows may be of, for example, 900 frames, corresponding to 1 minute at 15 frames per second. Successive time windows may be overlapping, for example by 0.9 seconds.

The invention may also be embodied in a computer program for processing a captured video image sequence in accordance with the invention and for outputting the results on a display. Such a computer program may run on a general purpose computer of conventional type.

DRAWINGS

FIG. 1 schematically illustrates a room containing a subject under monitoring in accordance with an embodiment of the invention;

FIG. 2 schematically illustrates one screen of a graphical user interface in one embodiment of the invention;

FIG. 3 schematically illustrates one screen of a graphical user interface in an embodiment of the invention;

DETAILED DESCRIPTION

Figure 1:
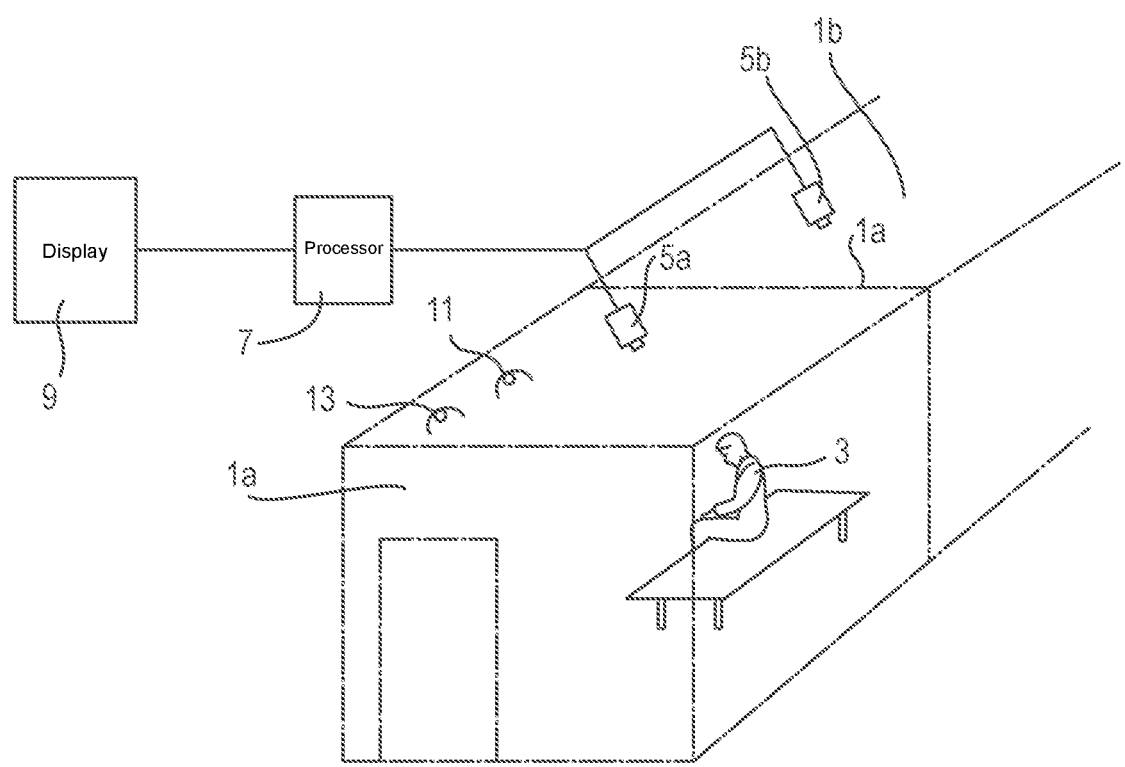

FIG. 1 schematically illustrates an apparatus in accordance with an embodiment of the invention being used to monitor a subject 3 in a room 1a. The room 1a can be a secure room such as a police or prison cell or some other detention facility, or could be a room in a hospital or other care facility such as a care home, sheltered accommodation or the subject's own home. It may be one of plural rooms being monitored as indicated by the neighbouring room 1b. The subject 3 is monitored by a video camera 5a whose output is processed by a video signal processor 7 and the results of the analysis are displayed on a display 9 which is visible to staff of the facility. The video signal processor 7 receives inputs from the video cameras 5b in other rooms. The video signal processor 7 may be a dedicated signal processor or a programmed general purpose computer. The rooms may be naturally lit or may be artificially illuminated using a visible light source 11 or infrared light source 13.

The video camera 5a,b is a standard digital video camera outputting video data in the form of a sequence of image frames, each frame being a pixel array of intensities in red, green, blue channels. The red, green and blue channels also give a response in the infrared range allowing the production of an infra-red (IR) image useful when the room is dark. Video cameras of this type typically output the signal at fifteen frames per second, though of course different frame rates are possible.

The display 9 preferably displays the video image of the rooms and also displays information regarding the health or safety of the subject 3. This information is preferably:

Whether movement is present.

Whether the subject is judged to be safe.

The time since the last vital signs observations were taken.

A no movement and no vital signs alert or alarm.

Staff monitoring the subject by way of the display 9 can therefore tell at any given time whether the subject is considered safe, for example because they are moving or because the vital signs are being detected and are in a physiologically normal range, or whether the system is unable to detect vital signs and safe movement is detected (and for how long that situation has persisted), or that no vital signs and no movement is present, in which case an alert is generated instructing staff to check the subject. If the lack of vital signs detection persists for more than a configurable amount of time an audio and/or visual alert may be generated to call on staff to check the subject. Alerts can include a range of electronic notification methods including automated telephone message, paper, SMS, as well as indication on the display 9 with the alert containing the condition and location of the subject and the condition being alerted.

Figure 4:
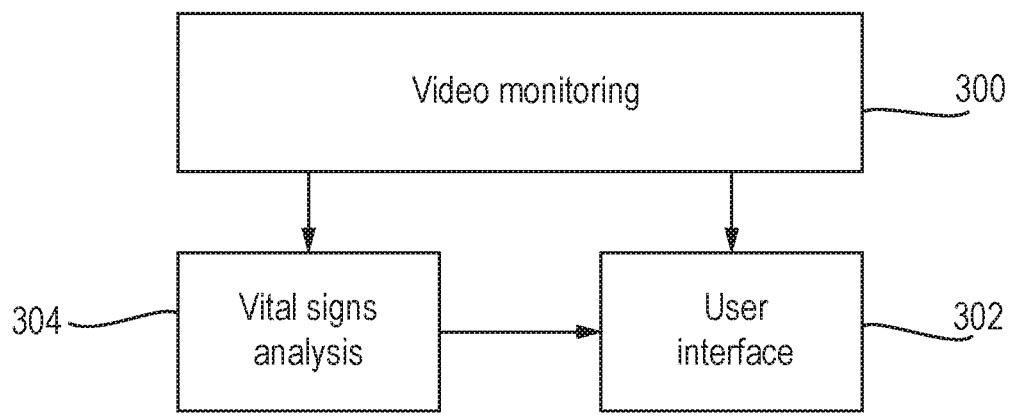
FIG. 4 is a flow diagram of the overall processing in one embodiment of the invention.

To estimate the vital signs, such as heart rate or breathing rate, from the video signals any of the published techniques based on analysing the image to detect a PPG signal may be used, e.g. those in WO-A2-2013/027027, WO-A-2011/021128 and WO-A1-2015/049150 or in "Distance PPG: robust non-contact vital signs monitoring using a camera" by Mayank Kumarthe which are incorporated herein by reference. These are typically based on detecting a photoplethysmogram signal and movements in video images of the subject and deriving the heart rate and breathing rate from this PPG signal and body movements associated with breathing. As schematically illustrated by FIG. 4, the vital signs estimation runs in a separate parallel process 304 on the processor 7 under the overall video monitoring process 300. Its output is provided to the user interface process 302. As these estimation techniques are known to the person skilled in the art they are not described in detail here.

If at any stage the processor 7 does not have enough signal data to estimate vital signs (for example because the system is starting from initialisation or because the subject has been moving grossly, which means that estimation would be required to be re-initialised), then a display message "acquiring vital signs" is shown on the display 9 in respect of that subject. If the process 304 is estimating vital signs then it is assessed whether these are valid current heart rate and breathing rate measurements. By valid, is meant within the normal physiological range for this vital sign. If there is no valid current heart rate or breathing rate then it is assessed whether there is a relatively recent, for example, less than 5 seconds old, valid heart rate or breathing rate estimate, and if so, then this will be used as the current heart rate or breathing rate for display via the user interface process 302.

As well as providing live monitoring information the system may also record and provide a summary report of the vital signs and any alerts raised during predetermined periods, e.g. daily, weekly, monthly, and/or for the complete period the subject is in the room.

Figure 2:
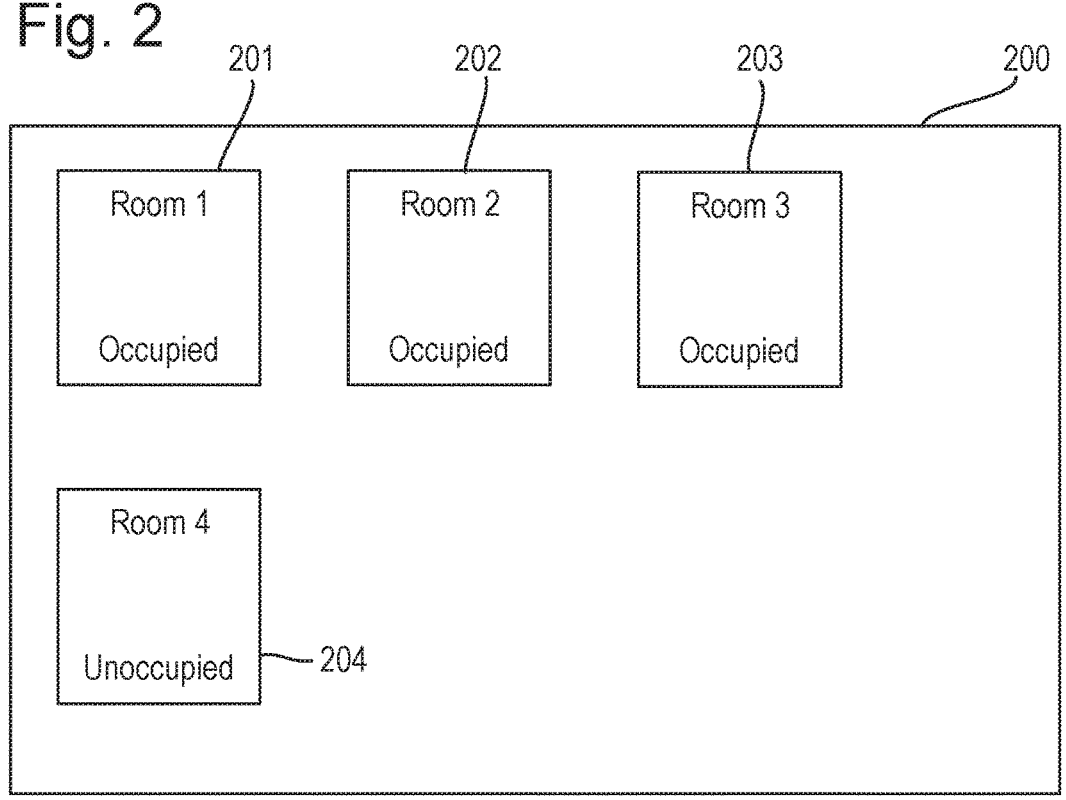

FIG. 2 schematically illustrates one screen of the graphical user interface 200 displayed on the display 9 by the user interface process 302. As illustrated in FIG. 2, in the graphical user interface 200, individual icons 201, 202, 203, 204 are displayed, each representing one of the rooms 1a, 1b . . . being monitored. In this embodiment each of the icons includes a label indicating which room it represents, and an indication of whether the room is occupied or unoccupied. Depending on the most convenient installation method, the indication of whether the room is occupied or unoccupied can be based on a sensor in the room, a user-controlled setting or analysis of camera frames to determine whether a person is present in the room.

Figure 3:
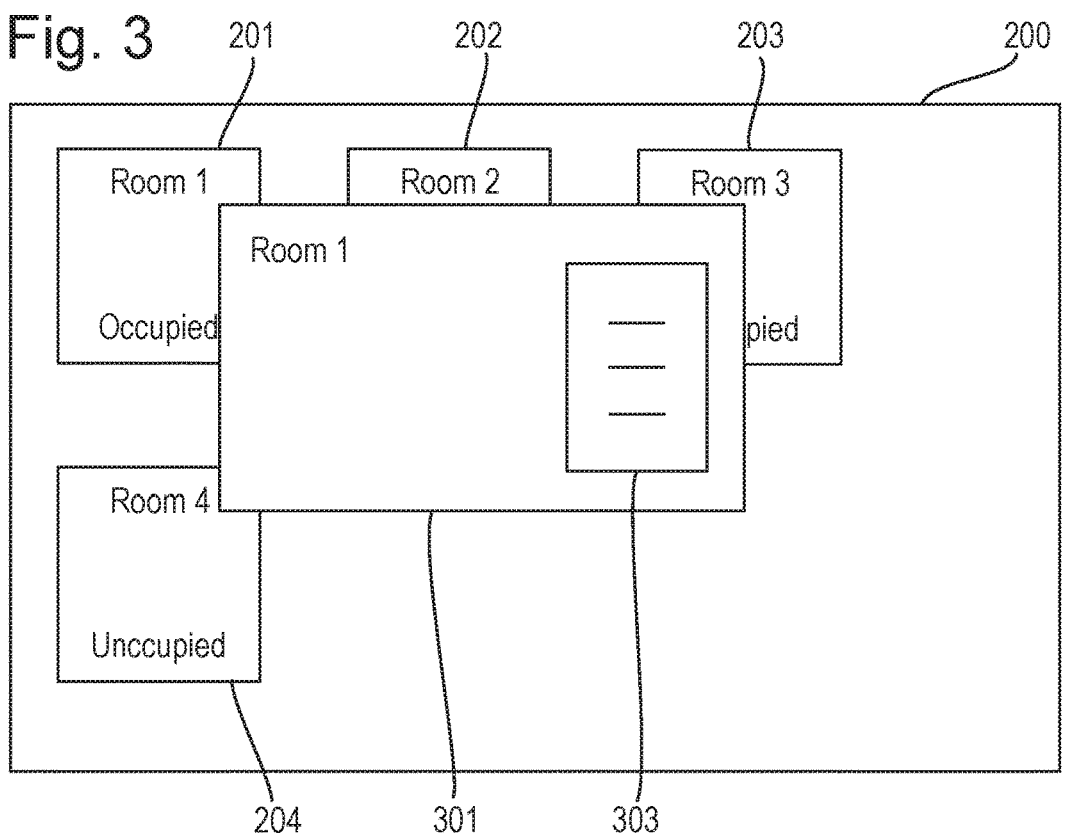
Figure 5:
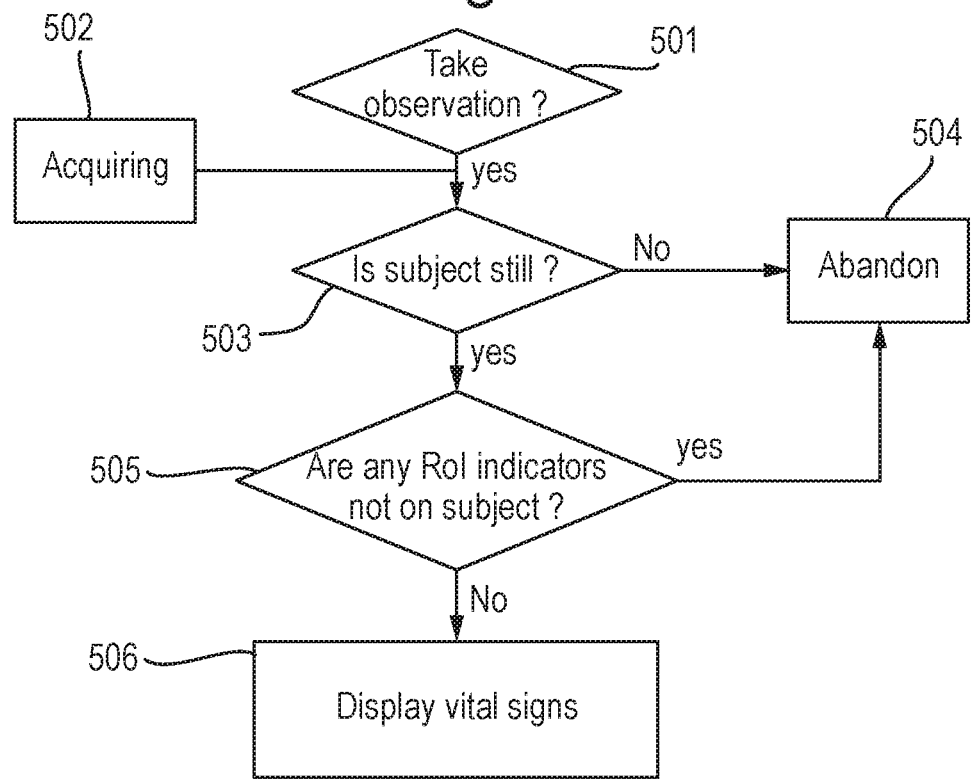
FIG. 5 is a flow diagram of the process flow in one embodiment of the invention.

FIG. 3 schematically illustrates a screen of the user interface 200 which is displayed on the display 9 in response to selection of one of the icons 201-204 of FIG. 2. As illustrated, an icon 301 is displayed overlying the display of FIG. 2, the icon 301 presenting a list of selectable options 303 for the user to choose. The selectable options include:
"Take an observation"
"View observation history", meaning to display to the user the previous vital signs measurements made in the past 24 hours One of the options in the list 303 is to "take an observation", meaning to display to the user the vital signs of the subject as obtained by the vital signs analysis process 304. FIG. 5 illustrates the process flow in response to selection of the "take an observation" option in FIG. 3.

In response to the user selecting the "take an observation" option in step 501, it is checked whether or not the vital signs analysis process 304 is currently returning a vital signs measurement. If not, then the message "acquiring" will be displayed on the display 9 in step 502.

If vital signs are present, or once they have been acquired, a determination will be made in step 503 as to whether the subject is still. This may be manual or automatic. In the manual embodiment the graphical user interface 200 displays the question "Is the subject still?" and offers clickable icons for the user to choose "Yes" or "No". The user makes the determination based on the displayed video image 302 and clicks the appropriate icon.

In the automatic embodiment a standard algorithm for detecting a human subject in an image such as the single shot detection algorithm is used, together with a standard algorithm for detecting movement of the subject such as calculating the differences in pixel values between frames over time, or using optical flow to track features in the frames and measuring the velocity with which the features move.

If the subject is not determined in step 503 as being still, it will mean that a vital signs measurement cannot be taken or will not be accurate and so the process is abandoned in step 504. Alternatively, if the subject is determined as still, then a determination is made in step 505 of whether the vital signs being detected by the vital signs analysis process 304 are all coming from regions of the image which are on the subject 3. Again, this can be performed manually or automatically.

Figure 6:
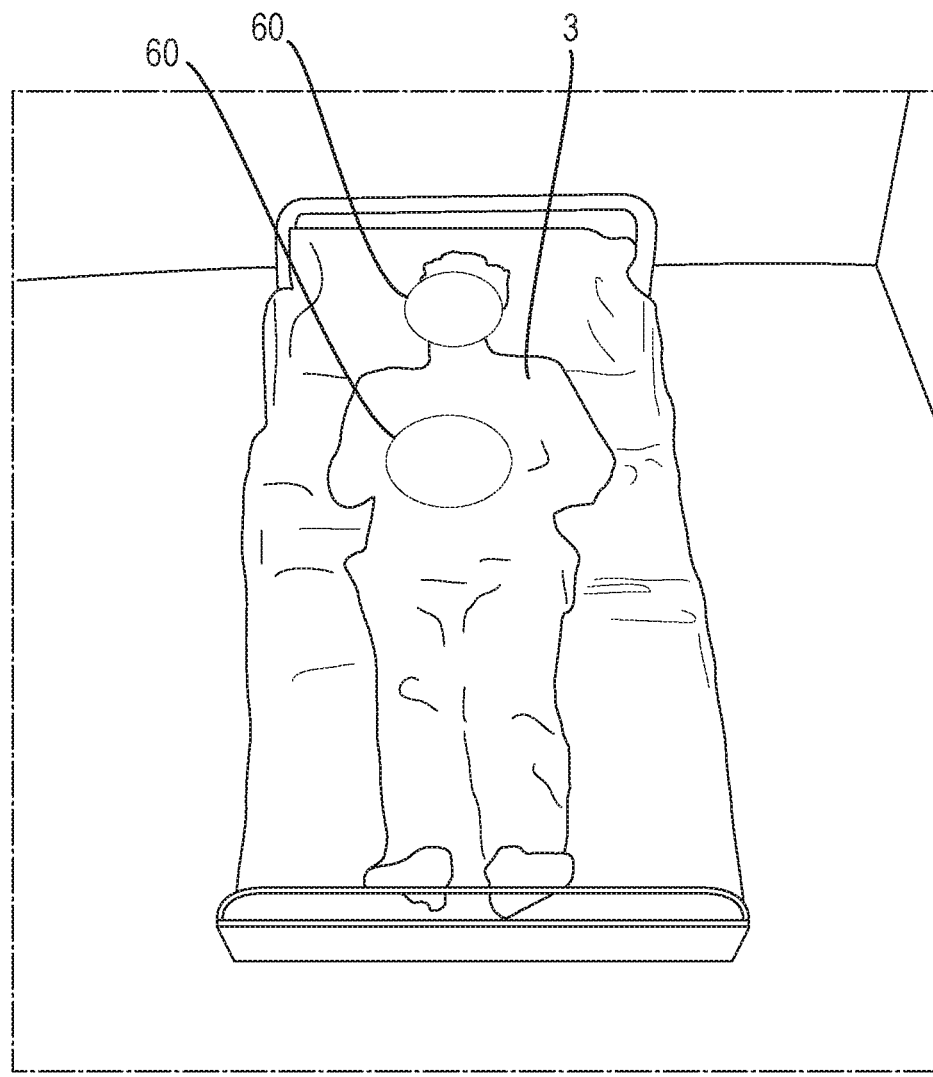
FIG. 6 is an example of a subject under monitoring, showing an image frame with circles indicating the areas from which vital signs are being measured.

In the manual embodiment, the processor 7 displays in the video image 302 the regions of the image from which vital signs are being detected by the vital signs analysis process 304. This may be by outlining them, or changing their intensity or colour, or displaying an icon overlying such regions. FIG. 6 shows an example display from a manual embodiment in which circles 60 indicate the regions from which vital signs are being detected. In FIG. 6, heart rate is being measured from the skin on the face of the subject 3, and breathing rate is being measured from movements of the chest and abdomen. The processor also displays a question to the user asking whether any of the displayed indicators are not on the subject and provides for clickable icons for the user to indicate "Yes" or "No" answers.

In the automatic embodiment, the processor uses automatic subject detection as above, and determines whether any of the regions from which the vital signs analysis process 304 is returning vital signs, are not on the automatically detected subject 3.

If any of the regions from which vital signs are being detected are not on the subject, this means that there are extraneous signal sources and the vital signs estimation is not reliable. Consequently the process abandons in step 504. Alternatively, if the only regions from which vital signs are detected are on the subject, it can be assumed that the vital signs measurements are meaningful and they are displayed on the display 9 in step 506.

The vital signs analysis process 304 may automatically find regions of interest in the video image from which vital signs are to be assessed, or may use user input to guide the selection of regions of interest. An example of an automated method is to calculate the "centre of mass" of a set of highly correlated vital sign signals found by the vital signs analysis process, weighted by the strength of the signals. The region of interest is then displayed as a circle whose radius indicates how spatially distributed these signals are. An example of a user-guided selection method is to require the user to first define the region of the image from which vital signs are to be measured (for example by drawing a rectangle over the chest region from which breathing rate is to be measured, or by drawing a rectangle over the whole of the subject's body).

Although the explanation above is on the basis of a subject detained in a secure room, the same technique may be used for monitoring the health and well-being of subjects in other environments such as hospitals or care homes, the home or workplace or in fitness or health facilities such as gyms and sports facilities.

The invention may be embodied in a signal processing method, or in a signal processing apparatus which may be constructed as dedicated hardware or by means of a programmed general purpose computer or programmable digital signal processor. The invention also extends to a computer program for executing the method.

The invention claimed is:

1. A method of monitoring a human or animal subject comprising the steps of:
    capturing a video image of the subject;
    analysing the video image to determine one or more vital signs detected on at least one of (i) the subject and (ii) a region excluding the subject;
    displaying to a user a graphical user interface comprising an icon indicative of the monitoring of the subject;
    determining whether the subject is still;
    if the subject is determined as still, determining based on input from the user whether all regions of the video image from which vital signs are detected are on the subject by displaying the video image of the subject with an indication in the video image of where vital signs are being detected and accepting user input to the graphical user interface indicating whether there are any regions of the image from which vital signs are being detected that are not on the subject; and
    only if the subject is determined as still and all regions of the video image from which vital signs are detected are on the subject, displaying the determined vital signs.

2. A method according to claim 1 further comprising:
    displaying a menu of selectable steps, one of said selectable steps being to take an observation of the vital signs of the subject; and
    upon selection of the step of taking an observation of the vital signs of the subject, performing said steps of determining whether the subject is still, and whether all regions of the video image from which vital signs are detected are on the subject.

3. A method according to claim 1 wherein the step of determining whether the subject is still comprises displaying the video image of the subject and displaying on the graphical user interface a request for the user to input to the graphical user interface the result of a user determination of whether the subject is still.

4. A method according to claim 1 wherein the step of determining whether the subject is still or moving comprises automatic determination of whether the subject is still.

5. A method according to claim 4 wherein the step of detecting the subject in the video image is performed using a single shot detection algorithm.

6. A method according to claim 1 wherein the step of displaying the video image of the subject with an indication in the video image of where vital signs are being detected comprises displaying regions of interest from which vital signs are being detected.

7. A method according to claim 6 wherein the regions of interest are displayed as circles whose centres indicate the centre of mass of a set of highly correlated vital sign signals.

8. A method according to claim 6 wherein the regions of interest are displayed as circles whose centres indicate the centre of mass of a set of highly correlated vital sign signals, weighted by the strength of the signals.

9. A method according to claim 7 wherein the radii of the circles indicate the spatial distribution of the signals.

10. A method according to claim 1 wherein the step of displaying the video image of the subject with an indication in the video image of where vital signs are being detected comprises displaying visual indicators in the image over areas of the video image from which vital signs are being detected.

11. A method according to claim 1 comprising monitoring a plurality of subjects simultaneously, and wherein the graphical user interface comprises a respective icon indicative of the monitoring of each of the respective subjects.

12. A system for monitoring a human or animal subject, comprising:
- a video camera adapted to capture a video image of the subject;
- a display;
- a video image processing unit adapted to: analyse the video image to determine one or more vital signs detected on at least one of (i) the subject and (ii) a region excluding the subject;
- display on the display a graphical user interface comprising an icon indicative of the monitoring of the subject;
- obtain a determination of whether the subject is still;
- if the subject is determined as still, determine based on input from the user whether all regions of the video image from which vital signs are detected are on the subject by displaying the video image of the subject with an indication in the video image of where vital signs are being detected and accepting user input to the graphical user interface indicating whether there are any regions of the image from which vital signs are being detected that are not on the subject;
- only if the subject is determined as still and all regions of the video image from which vital signs are detected are on the subject, display on the display the determined vital signs.

* * * * *